United States Patent [19]

Kropp

[11] 4,255,191

[45] Mar. 10, 1981

[54] GOLD-SILVER ALLOYS WITH GOOD TARNISH RESISTANCE FOR THE DENTAL ART

[75] Inventor: Rudolf Kropp, Pforzheim-Würm, Fed. Rep. of Germany

[73] Assignee: Degussa Aktiengesellschaft, Frankfurt am Main, Fed. Rep. of Germany

[21] Appl. No.: 123,071

[22] Filed: Feb. 20, 1980

[30] Foreign Application Priority Data

Mar. 2, 1979 [DE]  Fed. Rep. of Germany ....... 2908203

[51] Int. Cl.$^3$ ................................................. C22C 5/02
[52] U.S. Cl. .................................. 75/134 N; 75/165;
75/173 R
[58] Field of Search ................. 75/134 N, 165, 173 R

[56] References Cited

U.S. PATENT DOCUMENTS

| | | | |
|---|---|---|---|
| 3,819,366 | 6/1974 | Katz | 75/172 R |
| 3,925,073 | 12/1975 | Kohrn | 75/173 C |
| 4,007,040 | 2/1977 | Kropp | 75/165 |
| 4,008,080 | 2/1977 | Wagner | 75/134 N |
| 4,111,690 | 9/1978 | Harmsen | 75/165 |

FOREIGN PATENT DOCUMENTS

| | | |
|---|---|---|
| 2136232 | 1/1973 | Fed. Rep. of Germany . |
| 2139331 | 2/1973 | Fed. Rep. of Germany . |
| 2160721 | 6/1973 | Fed. Rep. of Germany . |
| 2509476 | 1/1979 | Fed. Rep. of Germany . |

*Primary Examiner*—R. Dean
*Assistant Examiner*—Upendra Roy
*Attorney, Agent, or Firm*—Cushman, Darby & Cushman

[57] ABSTRACT

Gold-silver alloys with good tarnish resistance for the dental art are prepared which, contrary to the known tarnish resistant alloys, still contain copper and thus have a deeper gold color and a high ductility. The alloys contain 33 to 48% gold, 0-5% platinum, 1-10% palladium, 0-0.2% iridium and/or ruthenium, 3-9% copper, 1-6% zinc, 0.5-4% tin and 2.5-10% indium, balance silver, wherein the mass ratio of copper to zinc is between 1:1 and 4:1, the content of copper is not higher than the sum of zinc, tin and indium, the content of palladium is at most three times as great as that of indium and does not exceed the sum of zinc, tin and indium. Under these provisions the copper content is not perceptibly disadvantageous to the resistance to discoloration.

13 Claims, No Drawings

GOLD-SILVER ALLOYS WITH GOOD TARNISH RESISTANCE FOR THE DENTAL ART

BACKGROUND OF THE INVENTION

The invention is directed to gold-silver alloys with good tarnish resistance for the dental art, particularly to castings of crowns, bridges and inlays. In connection therewith the metal additives are so chosen in their composition that danger of dark discolorations in the milieu of the mouth due to the addition of copper and/or silver is greatly reduced or entirely eliminated.

Gold alloys are preferred in the dental art for the production of crowns and bridges, which alloys for aesthetic reasons should be gold to light gold in color and whose hardness value after the casting for crowns should be at least 120 HV and for bridges at least 150 HV. This hardness value for a long time has been reached through addition of platinum metals and above all through addition of copper, which from the miscibility gap commencing from the system silver-copper makes possible a hardening mechanism in the crystal lattice by suitable heat treatment or by slow cooling after the casting. On the other hand copper containing alloys have the disadvantage that in the milieu of the mouth they lead to brown, black or bluish tarnish layers which mainly consist of copper sulfide and are strongly detrimental to the appearance of a prosthetic piece of work. This appearance occurs after a short carrying time in the mouth if there occurs a thin copper precipitate on the alloy surface because of local element formation which are discolored through the influence of sulfur containing compounds in the saliva and food. The copper comes from the copper containing solid solution crystal of the alloy, which is resistant itself. The copper diffuses out with oxide formation in the heating in air and collects on surface or in solidification cavities. It is true that this copper oxide goes into solution in the acidification, however, it can in using a non-noble metal forceps again deposit on the surface of the alloy. Besides the copper oxide on the inside of the cavities is frequently not dissolved out or only incompletely dissolved by acids, above all if cavities are first opened after the acidication of the cast piece through slipping of the cast piece. In those cases the copper oxide frequently first goes into solution in the course of weeks and months after incorporation of the piece in the mouth of the patients, during which local cells which form because of the differential aeration between inner and outer regions of the cavities lead to a further precipitation of copper ions as copper films in the vicinity of the cavity opening.

The danger of discoloration caused by the copper is eliminated if there is relinquished the inclusion of copper in the alloys and to produce the required hardness there is employed, in place of copper, additions of cobalt, iron and/or nickel (Kropp, German OS No. 2,136,232), indium tin and zinc (Wagner German AS No. 2,139,331) or increased additions of platinum and zinc (Kropp German AS No. 2,509,476 and related Kropp US.S Pat. No. 4,007,040). Alloys of the type mentioned have mouth and tarnish resistance but additions of cobalt iron and nickel exhibit the difficulty that the alloys are coated with oxide layers in the casting or annealing which are only dissolved with difficulty with the customary dilute acids (hydrochloric acid, dilute sulfuric acid or sulfamic acid) of the dental art. The increased addition of platinum leads to an undesired increase in cost of the alloys as well as to a relatively strong lightening of the gold color even at high gold contents. Both disadvantages above all are of importance if, to save expense, the gold content should not exceed a certain height. The complete elimination of the addition of copper in hard gold alloys which owe their hardness only to addition of platinum metals in combination with zinc, tin or indium proves disadvantageous in that the ductility of the copper free alloys is clearly lower than of the copper containing alloys, i.e., the danger from fractures by de- in formations is greater. Furthermore copper additions offer the advantage of a deeping of the gold color. For these reasons it is desirable in the dental art to use gold alloys which still contain a certain amount of copper, however, without the danger of a discoloration being exposed.

It is known that when pure copper is annealed in air it is coated with black copper oxide while copper-zinc alloys having a high zinc content (brass) with the same annealing treatment remain light, since in this case only white zinc oxide forms on the metal surface, while the formation of copper oxide is suppressed. The known gold dental alloys with relatively high amounts of copper and relatively low amounts of zinc upon annealing are coated with black copper oxide.

Furthermore, it is known that the susceptibility of silver and silver alloys to tarnish from sulfur compounds can be substantially reduced by additions of indium in combination with additions of tin and zinc (Harigaya, German OS No. 2,160,721) without the light silver color being impaired by a gray streak to a mentionable extent.

Therefore it was the problem of the present invention to provide gold-silver alloys with good tarnish resistant properties for the dental art, particularly for the casting of crowns, bridges and inlays which are relatively low in gold, nevertheless have a full gold color, are hard and nevertheless should be ductile.

SUMMARY OF THE INVENTION

This problem is solved according to the invention by using alloys which contain 33 to 48% gold, 0–5% platinum, 1–10% palladium, 0–0.2% iridium and/or ruthenium, 3–9% copper, 1–6% zinc, 0.5–4% tin and 2.5–10% indium, balance silver, wherein the mass ratio of copper to zinc is between 1:1 and 4:1, the content of copper is not higher than the sum of zinc, tin and indium, the content of palladium is at most three times as great as that of indium and does not exceed the sum of zinc, tin and indium. Preferably the mass ratio of copper:zinc is between 1:1 and 3:1 and the mass ratio of copper: sum of zinc, tin and indium is between 1:1 and 1:3.

Preferably in these alloys the sum of the content of gold, palladium, platinum, iridium and ruthenium is between 40 and 50%, the sum of these noble metals including silver is above 80%.

The preferred alloys contain 35–45% gold, 2–7% palladium, 0.5–2% platinum, 0.05–0.2% iridium and/or ruthenium, 4–8% copper, 2–4% zinc, 1–3% tin and 3–6% indium, balance silver.

For example it was established that cast parts of known alloys with about 40% gold, 40–45% silver, 2–7% platinum metals, 12–13% copper and 0–1% tin without other additives tarnish darkly when stored for several hours in 0.1 mol/1 Na$_2$S solution, in which case this effect especially clearly occurs with highly polished, cast parts which in the casting came out with porosities, i.e. under conditions such as occur for the most part in dental gold processing. In contrast the alloys of the invention with smaller copper contents and therefore higher zinc contents with simultaneous addition of indium and tin under the same test conditions remain light yellow. The prerequisite for this is that the mass ratio of copper: sum of zinc, tin and indium is at most 1:1. A further prerequisite is that the palladium content is not too high, i.e. the mass ratio of palladium: indium is permitted to be at most 3:1, the mass ratio of palladium: sum of indium, zinc and tin is at most 1:1, since otherwise the palladium forms with the mentioned none noble metals intermetallic compounds of higher heat of formation and therewith their effectiveness as inhibitors of the formation of copper oxide or copper or silver sulfide is reduced.

Experiments with various known gold platinum alloys containing additions of copper and zinc have shown that commercial alloys containing 9-11% copper and only about 1% zinc become black in the annealing, i.e. are coated with copper oxide, while an alloy of the invention with 9% copper and 6% zinc remains light and copper is not detected, even in traces, in the light, thin alloy layer in spite of the relatively high proportion of copper. Through experiments set forth in the Table it has been shown surprisingly that the copper content even can be increased up to a ratio of Cu:Zn=4:1 without the formation of CuO in the annealing or casting of the alloys, so long as the amount of copper does not exceed the amount of zinc and tin and indium.

Furthermore, it has been established that alloys containing about 34% silver or more and with contents of 35 to 45% of gold, about 1% platinum and 2 to 7% palladium with additions of 3 to 6% indium, 1 to 3% tin and 2 to 4% zinc are substantially more resistant to solutions of $Na_2S$ or $H_2S$ than alloys which do not contain these additives orr only contain 1% zinc as an additive.

Unless otherwise indicated all parts and percentages are by weight. The compositions can consist essentially of or consist of the materials set forth.

DESCRIPTION OF THE PREFERRED EMBODIMENTS

The table shows a series of alloys according to the invention and their properties. There were produced oxide layers on the surface of the alloy parts both by annealing sheets at 600° C. and also in the casting of full cast crowns. These layers were dissolved in dilute hydrochloric acid and the solution tested for copper ions. In these alloys there were found either no copper or only traces thereof.

In another test cast parts of the alloys set forth in the table were ground and polished and after pretreatment with a 0.1 mol/1 lactic acid and sodium chloride solution were treated with a 0.1 mol/1 sodium sulfide solution while simultaneously passing a current of air therethrough. They showed no discoloration. This test imitates the conditions in the milieu of the mouth where likewise lactic acid is formed through corresponding bacteria, sodium chloride is present at least part of the time and sulfide ions are formed by decomposition of the thiocyanate ions present in the saliva or from sulfur containing aminoacids.

The alloys of the invention behave in the mouth substantially more resistant to discoloration than those having a higher copper content or having lower zinc, tin and indium contents, wherein there is the additional separate advantage that this is also valid for alloys whose gold content is lower than was customary previously in the dental art.

The ductility of the gold dental alloys of the invention with an addition of copper is clearly improved over the copper free alloys obtainable in the trade. For example there were measured an elongation at fracture of 24% in the soft annealed condition and of 16% after the subsequent hardening compound compared to 13 to 21%, respectively 5 to 7% with copper-free alloys although the addition of zinc, tin and indium is higher with the first mentioned alloys.

It was surprisingly established with potential measurements with a highly sensitive galvanometer that in the immersion of the alloys of the invention together with a commercial gold dental alloy having more than 75% gold and platinum metals in 0.1 mol/1 lactic acid and 0.1 mol/1 NaCl solution there only resulted a potential difference of 10 to 25 mV although the portion of gold and platinum metals in the alloys of the invention was about 30% lower than in the high gold content dental alloy.

The resistance to dilute acids was tested on an alloy with altogether 17% non-noble metals. After storing samples for 17 days in a 1 to 4 diluted concentrated hydrochloric acid there was ascertained a weight loss between 0 and a maximum of 0.1 $mg/cm^2$. Since this test acid is substantially stronger than any acid occurring in the mouth there can be excluded any possible acid attach in vivo on the alloys of the invention.

TABLE

| Nr. | Au | Pt | Pd | Ir | Ru | Ag | Cu | Zn | Sn | In | Melting range °C. | CuO Formation | HV Cast |
|---|---|---|---|---|---|---|---|---|---|---|---|---|---|
| 1 | 35 | | 9 | | | 39 | 8 | 4 | 2 | 3 | 845-780 | — | 220 |
| 2 | 38 | 4 | 2 | | | 34.5 | 9 | 5 | 0.5 | 7 | 780-680 | — | 230 |
| 3 | 40 | 1 | 4.9 | 0.1 | | 42 | 4 | 2 | 2 | 4 | 905-775 | — | 180 |
| 4 | 40 | 1 | 5.9 | 0.1 | | 41 | 4 | 1 | 3 | 4 | 920-800 | — | 160 |
| 5 | 40 | 1 | 5.9 | 0.1 | | 40 | 4 | 2 | 2 | 5 | 900-795 | — | 175 |
| 6 | 40 | | 5.91 | | 0.09 | 41 | 4 | 2 | 2 | 5 | 895-795 | — | 180 |
| 7 | 40 | 1 | 5.9 | 0.1 | | 39 | 5 | 2 | 2 | 5 | 900-750 | — | 190 |
| 8 | 40 | 1 | 5.9 | 0.1 | | 38.5 | 5.5 | 2 | 2 | 5 | 880-730 | — | 195 |
| 9 | 40 | 1 | 5.9 | 0.1 | | 38 | 6 | 2 | 2 | 5 | 885-770 | — | 210 |
| 10 | 40 | 1 | 6 | | | 36 | 8 | 2 | 2 | 5 | 860-750 | — | 220 |
| 11 | 45 | | 2 | | | 37 | 3 | 3 | 1 | 9 | 800-660 | — | 110 |
| 12 | 48 | | 1 | | | 25 | 7 | 6 | 3 | 10 | 630-560 | — | 270 |

—: After the annealing or casting copper is either not detectable or only present in traces

What is claimed is:

1. A gold-silver alloy having good tarnish resistance and suitable for the dental art, particularly for the casting of crowns, bridges and inlays consisting essentially of 33 to 48% gold, 0–5% platinum, 1–10% palladium, 0–0.2% iridium or ruthenium or a mixture thereof, 3–9% copper, 1–6% zinc, 0.5–4% tin and 2.5–10% indium, balance silver, wherein the mass ratio of copper to zinc is between 1:1 to 4:1, the content of copper is not higher than the sum of zinc, tin and indium, the content of palladium is at most three times as great as that of indium and does not exceed the sum of zinc, tin and indium.

2. A gold-silver alloy according to claim 1 containing platinum.

3. A gold-silver alloy according to claim 2 free from iridium and ruthenium.

4. A gold-silver alloy according to claim 2 containing iridium or ruthenium or a mixture thereof.

5. A gold-silver alloy according to claim 1 free from platinum.

6. A gold-silver alloy according to claim 5 free from iridium and ruthenium.

7. A gold-silver alloy according to claim 5 containing iridium or ruthenium or a mixture thereof.

8. A gold-silver alloy according to claim 1 wherein the sum of the gold, platinum, palladium, iridium and ruthenium is at least 40% and at most 50% and the sum of these noble metals together with silver is at least 80%.

9. A gold-silver alloy according to claim 8 containing 35–45% gold, 0.5–2% platinum, 2–7% palladium, 0.05–2% iridium or ruthenium or a mixture thereof, 4–8% copper, 2–4% zinc, 1–3% tin and 3–6% indium, balance silver.

10. A gold-silver alloy according to claim 9 wherein the weight ratio of copper:zinc is between 1:1 and 3:1 and the weight ratio of copper:sum of zinc, tin and indium is between 1:1 and 1:3.

11. A gold-silver alloy according to claim 8 wherein the weight ratio of copper:zinc is between 1:1 and 3:1 and the weight ratio of copper:sum of zinc, tin and indium is between 1:1 and 1:3.

12. A gold-silver alloy according to claim 1 wherein the weight ratio of copper:zinc is between 1:1 and 3:1 and the weight ratio of copper:sum of zinc, tin and indium is between 1:1 to 1:3.

13. A gold-silver alloy according to claim 1 containing 35–45% gold, 0.5–2% platinum, 2–7% palladium, 0.05–0.2% iridium or ruthenium or a mixture thereof, 4–8% copper, 2–4% zinc, 1–3% tin and 3–6% indium, balance silver.

* * * * *